United States Patent [19]

Nickish et al.

[11] Patent Number: 4,584,288
[45] Date of Patent: Apr. 22, 1986

[54] 6,6-ETHYLENE-15,16-METHYLENE-3-OXO-17α-PREGN-4-ENE-21,17-CARBOLACTONES, PROCESSES FOR THE PRODUCTION THEREOF, AND PHARMACEUTICAL PREPARATIONS CONTAINING THEM

[75] Inventors: Klaus Nickish; Dieter Bittler; Henry Laurent; Rudolf Wiechert; Sybille Beier; Walter Elger, all of Berlin, Fed. Rep. of Germany

[73] Assignee: Schering Aktiengesellschaft, Berlin and Bergkamen, Fed. Rep. of Germany

[21] Appl. No.: 692,489

[22] Filed: Jan. 18, 1985

[30] Foreign Application Priority Data

Jan. 20, 1984 [DE] Fed. Rep. of Germany ....... 3402329

[51] Int. Cl.$^4$ .................... C07J 19/00; A61K 31/58
[52] U.S. Cl. ............................... 514/172; 260/239.57
[58] Field of Search .................... 260/239.57; 514/172

[56] References Cited

U.S. PATENT DOCUMENTS 3,422,097 1/1969 Kerwin ........................... 260/239.57
4,500,522 2/1985 Nickish et al. .................. 260/239.57

Primary Examiner—Elbert L. Roberts
Attorney, Agent, or Firm—Millen & White

[57] ABSTRACT 6,6-ethylene-15,16-methylene-3-oxo-17α-pregn-4-ene-21,17α-carbolactones of general Formula I

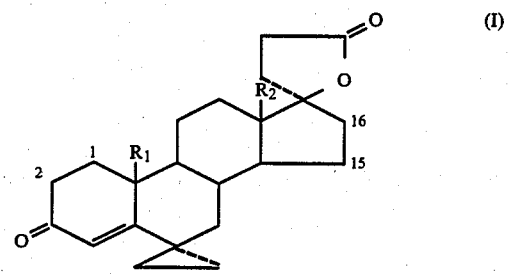

wherein

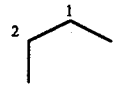

is a CC-single of CC-double bond,
$R_1$ is a hydrogen atom or a methyl group,
$R_2$ is a methyl or ethyl group, and

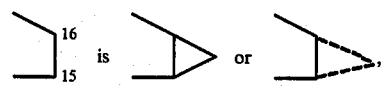

exhibit strong gestagen potency and an aldosterone-antagonistic activity.

18 Claims, No Drawings

6,6-ETHYLENE-15,16-METHYLENE-3-OXO-17α-PREGN-4-ENE-21,17-CARBOLACTONES, PROCESSES FOR THE PRODUCTION THEREOF, AND PHARMACEUTICAL PREPARATIONS CONTAINING THEM

BACKGROUND OF THE INVENTION

This invention relates to 6,6-ethylene-15,16-methylene-3-oxo-17α-pregn-4-ene-21,17-carbolactones, processes for the production thereof, and pharmaceutical preparations containing them.

SUMMARY OF THE INVENTION

It is an object of the invention to provide compounds having valuable pharmacological properties.

Upon further study of the specification and appended claims, further objects and advantages of this invention will become apparent to those skilled in the art.

These objects have been achieved by providing 6,6-ethylene-15,16-methylene-3-oxo-17α-pregn-4-ene-21,17-carbolactones of Formula I

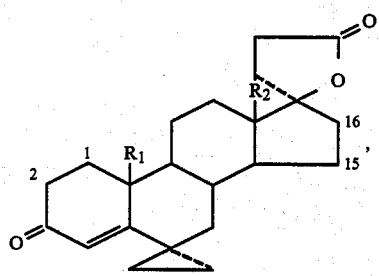

wherein

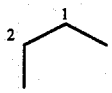

is a CC-single or CC-double bond,
$R_1$ is a hydrogen atom or a methyl group,
$R_2$ is a methyl or ethyl group, and

DETAILED DISCUSSION

The novel compounds of Formula I have, besides a high aldosterone-antagonistic activity, a strong gestagen potency. The combination of aldosterone-antagonistic and gestagen activities is not found in any of the known synthetic gestagens of the ethynylnortestosterone or hydroxyprogesterone series, but it does exist in the natural gestagen, namely progesterone. Since the novel compounds possess the progesterone-like profile of activity, they will not cause, when used as contraceptives, the otherwise occurring side effects, such as increases in blood pressure and edemas.

By replacing the ethylene group in the 6-position by a 6β,7β-methylene group, compounds are obtained which likewise show aldosterone-antagonistic and gestagen effects, but wherein the gestagen activity is not so strongly pronounced (DOS No. 3,022,337).

In a test for antialdosterone activity, the novel compounds of Formula I have proven to be up to five times more effective than spironolactone.

In the modified Clauberg test for gestagen activity, positive results are achieved with quantities of 0.03 mg of the compounds of this invention upon subcutaneous administration.

In the pregnancy-maintaining test on rats and mice, the minimum amount required for attaining a positive effect ranges around 0.1 mg.

The novel compounds of Formula I can be utilized by themselves or in combination with estrogens in preparations for contraception in fully conventional fashion, e.g., analogous to the use of conventional gestagens in these contraceptive preparations. According to this invention, the novel compounds are to be used particularly by women desiring contraception and prone to hypertension on account of risk factors present, such as advanced age, obesity, or smoking. Considering the profile of these compounds which is comparable to that of natural progesterone, they are apt to improve well-being and compatibility over conventional preparations even in women who cannot be classified as hish-risk patients. The dosage of the compounds of this invention on contraceptive preparations is to be preferably 0.5–5 mg per day. The gestagen and estrogen active agent components are administered in contraceptive preparations preferably orally in combination. The daily dose is administered preferably all at once as usual. The estrogen is administered daily in a quantity corresponding to that of 0.03–0.05 mg of ethynylestradiol.

The novel compounds of general Formula I can also be utilized in preparations for the treatment of gynecological disorders. Because of their favorable activity profile, the compounds of this invention are especially well suited for the treatment of premenstrual complaints, such as headaches, depressive moods, water retention, and mastodynia. The daily dose when treating premenstrual difficulties is about 1–20 mg, e.g., analogously to Duoluton®. They can also be used, analogously to spironalactone as diuretics and antihypertensives in the same dosis range as spironolactone.

The pharmaceutical preparations based on the novel compounds are formulated conventionally by processing the active agent, optionally in combination with an estrogen for contraception, with the excipients, diluents, if desired flavoring agents, etc., customary in galenic pharmacy, and converting this preparation into the desired form of administration. Tablets, dragees, capsules, pills, suspensions, or solutions are especially suitable for the preferred oral administration. Particularly suited for parenteral administration are oily solutions, e.g. solutions in sesame oil, castor oil, and cottonseed oil. To enhance solubility, solubilizers can be added, such as, for example, benzyl benzoate or benzyl alcohol.

Suitable hosts include mammals, including humans.

The compounds of this invention according to general Formula I can be prepared by conventionally introducing a 6α-hydroxy-methyl group into 15,16-methylene-3-oxo-17α-pregn-4-ene-21,17-carbolactones of general Formula II

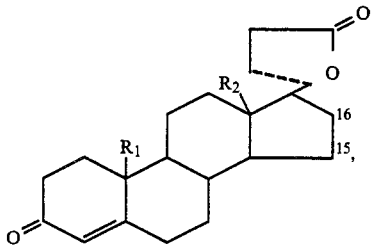 (II)

wherein

$R_1$ and $R_2$ are as defined for Formula I, by way of the 3,5-diene-3-amines using formalin, followed by reconstitution of the 4-ene-3-oxo system forming the 6-methylene compound from the 6α-hydroxymethyl compound. and methyenating this 6-methylene compound to the 6,6-ethylene compound, and optionally introducing the $\Delta^1$-double bond.

First of all, the $\Delta^4$-3-ketone is converted, with a secondary base, into the corresponding $\Delta^{3,5}$-3-amine. Suitable secondary bases are, for example, diethylamine, aniline, pyrrolidine, and morpholine.

For the introduction of the 6α-hydroxymethyl group, the $\Delta^{3,5}$-3-amine is treated with formalin in an alcoholic solution (Helv. Chim. Acta 56 (1973) 2396).

Water is split off from the 6α-hydroxymethyl compound with hydrochloric acid in dioxane, to obtain the corresponding 6-methylene compound. The water cleavage can also be performed by first introducing a fugacious group and splitting it off again. Suitable fugacious groups are, for example, mesylate, tosylate, and benzoate.

The methylenation of the 6-methylene compound to form the 6,6-ethylene compound can be effected in dimethylsulfoxonium methylide. For this purpose, the 6-methylene steroid is added to a suspension of trimethylsulfoxonium iodide with sodium hydride in mineral oil and dimethyl sulfoxide, or to a solution of trimethylsulfoxonium iodide and sodium hydroxide in dimethyl sulfoxide. The reaction is finished after 15–60 minutes at 20°–40° C. Corresponding reactions are described in J. Am. Chem. Soc. 84 (1962) 866–868.

The optionally following introduction of the $\Delta^1$-double bond is conducted according to methods known per se and can be done by chemical or microbiological processes. Suitable chemical dehydrogenating agents include, for example, selenium dioxde, 2,3-dichloro-5,6-dicyanobenzoquinone, chloranil, thallium triacetate, or lead tetraacetate. Suitable microorganisms for the 1,2-dehydrogenation include, for example, Schizomycetes, especially those of the genera Arthobacter, e.g. *A. simplex* (ATCC 6946); Bacillus, such as, for example, *B.lentus* (ATCC 13805) and *B. sphaericus* (ATCC 7055); Pseudomonas, e.g. *P. aeruginosa* (IFO 3505); Flavobacterium, e.g. *F. flavescens* (IFO 3058); Lactobacillus, e.g., *L. brevis* (IFO 3345); and Nocardia, e.g. *N. opaca* (ATCC 4276).

The 1,2-dehydrogenation is preferably performed chemically. For this purpose, the 1,2-dihydro steroid is heated for a rather long time in a suitable solvent with the dehydrogenating agent. Suitable solvents include, for example, dioxane, tert-butanol, tetrahydrofuran, toluene, benzene and/or mixtures of these solvents. The reaction is finished after several hours. It is recommended to control the conversion by thin-layer chromatography. The reaction mixture is worked up once the starting material has been converted.

The starting materials of Formula II are all known or readily preparable from known starting materials using conventional reactions, e.g., analogously to the preparations reported in Examples 5 and 6 below.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius. unless otherwise indicated, all parts and percentages are by weight.

EXAMPLE 1

(a) A solution of 4.1 g of 15β,16β-methylene-3-oxo-17α-pregn-4-ene-21,17-carbolactone in 31 ml of methanol is heated under reflux with 2.05 ml of pyrrolidine for 15 minutes. After cooling in an ice bath, the thus-formed precipitate is suctioned off, washed with a small amount of methanol, and dried, thus obtaining 4.5 g of 15β,16β-methylene-3-pyrrolidino-17α-pregna-3,5-diene-21,17-carbolactone, mp 234°–237° C. (with decomposition).

UV: $\epsilon_{276} = 22,900$.

(b) At room temperature, 4.5 ml of 37% strength formalin solution is added dropwise within 5 minutes to a solution of 4.5 g of 15β,16β-methylene-3-pyrrolidino-17α-pregna-3,5-diene-21,17-carbolactone in 90 ml of ethanol and 45 ml of benzene. After a reaction period of 30 minutes, the reaction solution is evaporated to dryness under vacuum. The residue is chromatographed on silica gel, thus producing 3.15 g of 6α-hydroxymethyl-15β,16β-methylene-3-oxo-17α-pregn-4-ene-21,17-carbolactone as an oil.

UV: $\epsilon_{241} = 14,500$.

(c) At room temperature, 3.15 g of 6α-hydroxymethyl-15β,16β-methylene-3-oxo-17α-pregn-4-ene-21,17-carbolactone is agitated for 2 hours in 77 ml of dioxane with 9.1 ml of 5N hydrochloric acid. The reaction solution is then combined with an excess of sodium bicarbonate, filtered off from the precipitated inorganic salts; the filtrate is diluted with ether and washed with water. After drying and evaporation, the residue is chromatographed on silica gel. Recrystallization from diisopropyl ether/acetone yields 1.2 g of 6;15β,16β-dimethylene-3-oxo-17α-pregn-4-ene-21,17-carbolactone, mp 173.1° C.

UV: $\epsilon_{261} = 11,300$.

(d) At room temperature, 1.41 g of trimethylsulfoxonium iodide is agitated for 1.5 hours with 239 mg of sodium hydride (55% oil suspension) in 21.5 ml of dimethyl sulfoxide (DMSO). Under argon, 1.14 g of 6;15β,16β-dimethylene-3-oxo-17α-pregn-4-ene-21,17-carbolactone is added to this solution, and the latter is stirred for 50 minutes at room temperature. The reaction solution is then stirred into ice water, weakly acidified with 2N sulfuric acid; the thus-formed precipitate is filtered off and taken up in methylene chloride. After drying and evaporation, the residue is chromatographed on silica gel. Recrystallization from diisopropyl ether/acetone yields 725 mg of 6,6-ethylene-15β,16β-methylene-3-oxo-17α-pregn-4-ene-21,17-carbolactone, mp 184.2° C.

UV: $\epsilon_{248} = 14,150$.

EXAMPLE 2

A solution of 670 mg of 6,6-ethylene-15β,16β-methylene-3-oxo-17α-pregn-4-ene-21,17-carbolactone and 670 mg of 2,3-dichloro-5,6-dicyano-p-benzoquinone in 13.4 ml of toluene is stirred for 5 hours at 100° C. The reaction solution is then diluted with ether, washed with water, sodium bicarbonate solution and water, dried, and evaporated. The residue is then chromatographed on silica gel. After recrystallization from diisopropyl ether/acetone, 445 mg of 6,6-ethylene-15β,16β-methylene-3-oxo-17α-pregna-1,4-diene-21,17-carbolactone is obtained, mp 199.7° C.

UV: $\epsilon_{243} = 15,150$.

EXAMPLE 3

(a) As described in Example 1, 5.9 g of 15α,16α-methylene-3-oxo-17α-pregn-4-ene-21,17-carbolactone is reacted in 40 ml of methanol with 2.95 ml of pyrrolidine and worked up, thus obtaining 5.9 g of 15α,16α-methylene-3-pyrrolidino-17α-pregna-3,5-diene-21,17-carbolactone, mp 235°–237.5° C. (with decomposition).

UV: $\epsilon_{276} = 23,300$.

(b) As described in Example 1, 5.9 g of 15α,16α-methylene-3-pyrrolidino-17α-pregna-3,5-diene-21,17-carbolactone is reacted in 118 ml of ethanol and 59 ml of benzene with 5.9 ml of 37% formalin solution and worked up, yielding 3.7 g of 6α-hydroxymethyl-15α,1-6α-methylene-3-oxo-17α-pregn-4-ene-21,17-carbolactone.

(c) 3.7 g of 6α-hydroxymethyl-15α,16α-methylene-3-oxo-17α-pregn-4-ene-21,17-carbolactone is agitated in 90.5 ml of dioxane with 10.7 ml of 5N hydrochloric acid for 3.5 hours at room temperature. The mixture is then worked up and purified as described in Example 1. After recrystallization from diisopropyl ether/acetone, 2.26 g of 6;15α,16α-dimethylene-3-oxo-17α-pregn-4-ene-21,17-carbolactone is obtained, mp 162.5°–163.5° C.

UV: $\epsilon_{262} = 11,300$.

(d) 1.87 g of 6;15α,16α-dimethylene-3-oxo-17α-pregn-4-ene-21,17-carbolactone is reacted, as described in Example 1, in 35 ml of DMSO with 2.31 g of trimethylsulfoxonium iodide and 393 mg of sodium hydride (55% oil suspension) and worked up. Recrystallization from diisopropyl ether/acetone yields 1.1 g of 6,6-ethylene-15α,16α-methylene-3-oxo-17α-pregn-4-ene-21,17-carbolactone, mp 176.6° C.

UV: $\epsilon_{247} = 13,900$.

EXAMPLE 4

At 80° C., 600 mg of 6,6-ethylene-15α,16α-methylene-3-oxo-17α-pregn-4-ene-21,17-carbolactone is stirred in 12 ml of toluene with 600 mg of 2,3-dichloro-5,6-dicyano-p-benzoquinone for 17 hours. The mixture is then worked up and purified as set forth in Example 3, thus obtaining 520 mg of 6,6-ethylene-15α,16α-methylene-3-oxo-17α-pregna-1,4-diene-21,17-carbolactone as an oil.

UV: $\epsilon_{242} = 14,600$.

EXAMPLE 5

(a) As described in Example 1, 5.0 g of 18-methyl-15β,16β-methylene-3-oxo-19-nor-17α-pregn-4-ene-21,17-carbolactone is reacted in 125 ml of methanol with 2.5 ml of pyrrolidine and worked up. Yield: 5.0 g of 18-methyl-15β,16β-methylene-3-pyrrolidino-19-nor-17α-pregna-3,5-diene-21,17-carbolactone.

(b) As described in Example 1, 5.0 g of 18-methyl-15β,16β-methylene-3-pyrrolidino-19-nor-17α-pregna-3,5-diene-21,17-carbolactone is reacted in 100 ml of ethanol and 50 ml of benzene with 5 ml of 37% formalin solution and worked up, thus obtaining 2.33 g of 6α-hydroxymethyl-18-methyl-15β,16β-methylene-19-nor-17α-pregn-4-ene-21,17-carbolactone as an oil.

UV: $\epsilon_{239} = 13,200$.

(c) At room temperature, 372 mg of 6α-hydroxymethyl-18-methyl-15β,16β-methylene-19-nor-17α-pregn-4-ene-21,17-carbolactone is stirred for 17 hours in 3.7 ml of pyridine with 572 mg of p-toluenesulfonic acid chloride. Then 0.09 ml of water is added, the mixture is further stirred for one hour at room temperature, and the reaction solution is stirred into ice water. The thus-formed precipitate is filtered off, washed with water, and taken up in methylene chloride. After drying and evaporation, 465 mg of 18-methyl-15β,16β-methylene-6α-tosyloxymethyl-19-nor-17α-pregn-4-ene-21,17-carbolactone is obtained as an oil.

UV: $\epsilon_{226} = 20,600$.

(d) A solution of 426 mg of trimethylsulfoxonium iodide in 15 ml of DMSO is combined with 72 mg of sodium hydride (55% oil suspension) and agitated for one hour at room temperature. Then, under argon, 300 mg of 18-methyl-15β,16β-methylene-6α-tosyloxymethyl-19-nor-17α-pregn-4-ene-21,17-carbolactone is added to this solution, the latter is stirred for another 15 minutes, and precipitated into ice water. The precipitate is filtered off, taken up in ether, washed with water, dried, and evaporated. Preparative thin-layer chromatography yields 145 mg of 6,6-ethylene-18-methyl-15β,16β-methylene-3-oxo-19-nor-17α-pregn-4-ene-21,17-carbolactone, mp 165.4° C.

UV: $\epsilon_{247} = 14,650$.

The starting compound according to 5(a) is prepared as follows:

A solution of 102 g of 15α-hydroxy-18-methyl-4-estrene-3,17-dione in 500 ml of pyridine is combined under ice cooling with 50.9 ml of benzoyl chloride and stirred for one hour under cooling. Then 9 ml of water is added dropwise and the mixture is stirred for another hour. The reaction solution is then stirred into ice water, the thus-formed precipitate is suctioned off, washed with water, and dried, thus obtaining 146 g of crude 15α-benzoyloxy-18-methyl-4-estrene-3,17-dione.

A solution of 146 g of 15α-benzoyloxy-18-methyl-4-estrene-3,17-dione in 1.46 l of dichloromethane is combined with 441 ml of ethylene glycol, 294 ml of orthoformic acid triethyl ester, and 7.3 g of p-toluenesulfonic acid and stirred for 1 hour at 50° C. Then, 20 ml of pyridine is added, the mixture is diluted with ether and washed with water. After drying and evaporation, 165 g of crude 15α-benzoyloxy-3,3-ethylenedioxy-18-methyl-5- or -5(10)-estren-17-one is obtained.

A solution of 320 g of trimethylsulfoxonium iodide in 1.5 l of DMSO is combined with 56.3 g of pulverized sodium hydroxide, and the mixture is stirred for 2.5 hours at room temperature. Under water cooling, 165 g of 15α-benzoyloxy-3,3-ethylenedioxy-18-methyl-5- or -5(10)-estren-17-one in 300 ml of DMSO is then added thereto and the mixture is stirred for 45 minutes. The reaction solution is then stirred into ice water, the thus-produced precipitate is filtered off, taken up in ether, washed with water, and dried. The residue obtained after evaporation is chromatographed on silica gel, yielding 79.2 g of 3,3-ethylenedioxy-18-methyl-15β,16β-methylene-5- or -5(10)-estren-17-one as an oil.

A solution of 62 g of 3,3-ethylenedioxy-18-methyl-15β,16β-methylene-5- or -5(10)-estren-17-one in 600 ml of absolute tetrahydrofuran (THF) is cooled to −10° C.; then, under argon, 186 g of potassium ethylate is added and thereafter 124 ml of distilled propargyl alcohol is added dropwise. The reaction solution is further agitated under cooling for 45 hours and then stirred into ice water, acidified with dilute sulfuric acid, and extracted with dichloromethane. After drying and evaporation, the residue is chromatographed on silica gel, thus obtaining 23 g of 3,3-ethylenedioxy-17α-(3-hydroxy-1-propynyl)-18-methyl-15β,16β-methylene-5- or -5(10)-estren-17β-ol as an oil.

A solution is prepared from 23 g of 3,3-ethylenedioxy-17α-(3-hydroxy-1-propynyl)-18-methyl-15β,16β-methylene-5- or -5(10)-estren-17β-ol in 150 ml of 2-propanol and 150 ml of THF and hydrogenated with hydrogen in the presence of 23 g of Raney nickel catalyst. The mixture is then filtered off from the catalyst and the filtrate evaporated to dryness. As the residue, 23 g of crude 3,3-ethylenedioxy-17α-(3-hydroxypropyl)-18-methyl-15β,16β-methylene-5- or -5(10)-estren-17β-ol is obtained in the form of an oil.

23 g of 3,3-ethylenedioxy-17α-(3-hydroxypropyl)-18-methyl-15β,16β-methylene-5- or -5(10)-estren-17β-ol is stirred in 230 ml of dimethylformamide (DMF) with 69 g of pyridinium dichromate for 24 hours at room temperature. The reaction solution is then stirred into ethyl acetate, suctioned off from the precipitated chromium salts, and the filtrate is washed with water. After evaporation, the residue is chromatographed on silica gel, yielding 15 g of 3,3-ethylenedioxy-18-methyl-15β,16β-methylene-19-nor-17α-pregn-5- or -5(10)-ene-21,17-carbolactone as an oil.

15 g of 3,3-ethylenedioxy-18-methyl-15β,16β-methylene-19-nor-17α-pregn-5- or -5(10)-ene-21,17-carbolactone is agitated for 6 hours at room temperature in 150 ml of methanol with 15 ml of 8 vol-% sulfuric acid. The reaction solution is then diluted with ether, washed with water, dried, and evaporated. The residue is chromatographed on silica gel and, after recrystallizing from diisopropyl ether/acetone, 8.5 g of 18-methyl-15β,16β-methylene-3-oxo-19-nor-17α-pregn-6-ene-21,17-carbolactone is obtained, mp 202.5°–205.5° C.

UV: $\varepsilon_{240} = 17{,}400$.

EXAMPLE 6

(a) A solution of 4.0 g of 15β,16β-methylene-19-nor-3-oxo-17α-pregn-4-ene-21,17-carbolactone in 35 ml of boiling methanol is combined with 2 ml of pyrrolidine and heated for another 20 minutes under reflux. After cooling, the thus-formed precipitate is suctioned off and washed with a small amount of cold methanol and dried under vacuum, yielding 4.3 g of 15β,16β-methylene-19-nor-3-pyrrolidino-17α-pregna-3,5-diene-21,17-carbolactone.

(b) 4.3 ml of formalin solution is added dropwise to a solution of 4.3 g of 15β,16β-methylene-3-pyrrolidino-19-nor-17α-pregna-3,5-diene-21,17-carbolactone in 43.6 ml of benzene and 87.2 ml of ethanol; the mixture is stirred for one hour at room temperature and concentrated under vacuum. The resultant crude product is chromatographed on silica gel, thus obtaining 1.9 g of 6α-hydroxymethyl-15β,16β-methylene-3-oxo-19-nor-17α-pregn-4-ene-21,17-carbolactone, mp 246.9° C.

(c) A solution of 2.06 g of 6α-hydroxymethyl-15β,16β-methylene-3-oxo-19-nor-17α-pregn-4-ene-21,17-carbolactone in 20 ml of pyridine is combined with 3.14 g of p-toluenesulfonic acid chloride; the mixture is stirred for 3 hours at room temperature, combined with 0.2 ml of water, agitated for another hour, and the reaction solution is precipitated into ice water. The resultant precipitate is filtered off, washed with water, and dried, yielding 2.39 g of 15β,16β-methylene-3-oxo-6α-tosyloxymethyl-19-nor-17α-pregn-4-ene-21,17-carbolactone.

(d) A solution of 3.84 g of trimethylsulfoxonium iodide in 75 ml of dimethyl sulfoxide is combined with 566 mg of 55% strength sodium hydride and agitated for one hour at room temperature. To this solution is added dropwise 2.36 g of 15β,16β-methylene-3-oxo-6α-tosyloxymethyl-19-nor-17α-pregn-4-ene-21,17-carbolactone in 2 ml of dimethyl sulfoxide; the mixture is agitated for 30 minutes and precipitated into ice water. The resultant crude product is chromatographed on silica gel, thus producing 985 mg of 6,6-ethylene-15β,16β-methylene-3-oxo-19-nor-17α-pregn-4-ene-21,17-carbolactone, mp 211°–214° C.

The starting compound according to 6(aa) is prepared as follows:

A solution of 69.2 g of 15α-hydroxy-4-estrene-3,17-dione in 408 ml of pyridine is combined under ice cooling with 46.4 ml of benzoyl chloride and stirred for one hour under cooling. Then the mixture is combined with 5.7 ml of water and agitated for 3 hours at room temperature and precipitated into ice water. The thus-formed precipitate is filtered off, washed with water, and dried, thus yielding 98.7 g of 15α-benzoyloxy-4-estrene-3,17-dione.

A solution of 98.7 g of 15α-benzoyloxy-4-estrene-3,17-dione in 4.5 l of dichloromethane is combined at 0° C. with 266.7 ml of ethylene glycol, 177.8 ml of orthoformic acid triethyl ester, and 889 mg of p-toluenesulfonic acid and agitated for 2.5 hours at this temperature. Thereafter the mixture is combined with some pyridine and washed repeatedly with water. After drying over magnesium sulfate, the mixture is concentrated under vacuum. The thus-obtained crude product is chromatographed on silica gel, yielding 69.1 g of 15α-benzoyloxy-3,3-ethylenedioxy-5- or -5(10)-estren-17-one.

A solution of 47.0 g of trimethylsulfoxonium iodide in 1 liter of dimethyl sulfoxide is combined with 18.4 g of 55% sodium hydride and agitated for one hour under argon. A solution of 69.1 g of 15α-benzoyloxy-3,3-ethylenedioxy-5- or -5(10)-estren-17-one is added dropwise thereto, and the mixture is further stirred at room temperature for one hour. Subsequently the reaction solution is stirred into ice water, the resultant precipitate is filtered off and dried. The thus-obtained crude product is chromatographed on aluminum oxide, yielding 41.5 g of 3,3-ethylenedioxy-15β,16β-methylene-5- or -5(10)-estren-17-one as an oil.

A solution of 41.5 g of 3,3-ethylenedioxy-15β,16β-methylene-5- or -5(10)-estren-17-one in 800 ml of tetrahydrofuran is combined at 0° C. under argon with 148 g of potassium ethylate and then with a solution of 57 ml of propargyl alcohol in 57 ml of tetrahydrofuran and further agitated for 2.5 hours at room temperature.

Then the mixture is acidified with sulfuric acid, diluted with water, extracted with ethyl acetate, and washed neutral with water. After drying and concentration under vacuum, the residue is chromatographed on silica gel, thus producing 38.0 g of 17β-hydroxy-17α-(3-hydroxy-1-propynyl)-15β,16β-methylene-4-estren-3-one, mp 161.3° C.

A solution of 38.0 g of 17β-hydroxy-17α-(3-hydroxy-1-propynyl)-15β,16β-methylene-4-estren-3-one in 1 liter of tetrahydrofuran is hydrogenated with 5.0 g of tris-triphenylphosphine rhodium(I) chloride and then concentrated under vacuum. Yield: 43.0 g of 17β-hydroxy-17α-(3-hydroxypropyl)-15β,16β-methylene-4-estren-3-one.

A solution of 43.0 g of 17β-hydroxy-17α-(3-hydroxypropyl)-15β,16β-methylene-4-estren-3-one in 1.4 g of dimethylformamide is combined with 160 g of pyridine dichromate and stirred overnight at room temperature. The reaction solution is subsequently stirred into 7 l of ethyl acetate, suctioned off from the precipitated chromium salts, and the filtrate is washed with water. After evaporation, the residue is chromatographed on silica gel, thus obtaining 22.5 g of 15β,16β-methylene-19-nor-3-oxo-17α-pregn-4-ene-21,17-carbolactone, mp 191.2° C.

EXAMPLE OF THE COMPOSITION OF A CONTRACEPTIVE TO BE ADMINISTERED ORALLY IN THE FORM OF A DRAGEE

| Core: | 2.000 mg | 6,6-Ethylene-15β,16β-methylene-3-oxo-17α-pregn-4-ene-21,17-carbolactone |
| --- | --- | --- |
| | 0.050 mg | Ethynylestradiol |
| | 31.100 mg | Lactose |
| | 18.000 mg | Corn starch |
| | 2.100 mg | Poly-N—vinylpyrrolidone |
| | 1.650 mg | Talc |
| | 0.100 mg | Magnesium stearate |
| | 55.000 mg | Total weight, which is filled up to about 90 mg with the usual sucrose mixture (coat) |

PHARMACOLOGICAL OBSERVATIONS

The antialdosterone activity is determined and measured in the test odel by Hollmann (G. Hollmann et al., "Tubulaere Wirkungen und renale Elimination von Spironolactonen" [Tubular Effects and Renal Elimination of Spironolactones], Naunyn-Schmiedebergs Arch. Exp. Path. Pharmak. 247: 419 [1964]; P. Marx, "Renale Wirkungen des d-Aldosterons und seines Antagonisten Spironolacton" [Renal Effects of d-Aldosterone and Its Antagonist Spironolactone], Diss. Med. Fak. FU Berlin, 1966).

The results of gestagen activity are obtained in the Caluberg test with subcutaneous administration of the active agents to castrated female rabbits. In the histological sections, the secretory conversion of the endometrium is determined. Evaluation is performed according to the McPhail scale (evaluation grades 1–4; 1=no conversion; 4=complete conversion).

In the pregnancy maintaining test on rats, the number of living and dead fetuses is determined after subcutaneous administration of the test compounds from the 8th to 21st day of gravidity, and the percentage of pregnancies maintained is calculated.

As can be seen from the table below, the compounds of this invention 2 and 3 show, with a good aldosterone-antagonistic activity, a stronger gestagen potency than the comparison compound 1.

| No. | Compound | Antialdosterone Test p.o. (Spironolactone = 1) | Clauberg Test s.c. | | Pregnancy Maintaining Test s.c. | |
| --- | --- | --- | --- | --- | --- | --- |
| | | | Dose [mg] | McPhail Value | Dose [mg] | % |
| 1 | 6β,7β;15β,16β-Dimethylene-3-oxo-17α-pregn-4-ene-21,17-carbolactone (Comparison) | 5–7 | 1 | 3.2 | 3 | 85 |
| | | | 0.3 | 2.1 | 1 | 74 |
| | | | 0.1 | 1.1 | 0.3 | 3 |
| | | | | | 0.1 | 0 |
| 2 | 6,6-Ethylene-15β,16β-methylene-3-oxo-17α-pregn-4-ene-21,17-carbolactone | 5 | 0.3 | 2.9 | 0.1 | 60 |
| | | | 0.1 | 2.6 | 0.03 | 11 |
| | | | 0.03 | 1.3 | 0.01 | 0 |
| 3 | 6,6-Ethylene-15β,16β-methylene-3-oxo-19-nor-17α-pregn-4-ene-21,17-carbolactone | 1 | 0.3 | 2.8 | | |

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 6,6-Ethylene-15,16-methylene-3-oxo-17α-pregn-4-ene-21,17-carbolactone of the formula

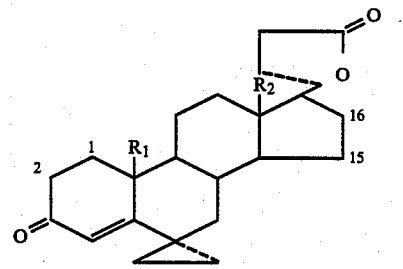

wherein

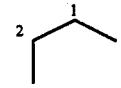

is a CC-single or CC-double bond,
R₁ is hydrogen or methyl,
R₂ is methyl or ethyl, and

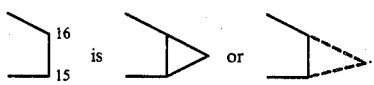

2. A compound of claim 1 wherein

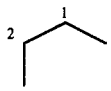

is a CC-single bond.

3. A compound of claim 1 wherein

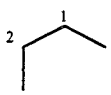

is a CC-double bond.

4. A compound of claim 1 wherein R₁ is H.
5. A compound of claim 1 wherein R₁ is CH₃.
6. 6,6-Ethylene-15β,16β-methylene-3-oxo-17α-pregn-4-ene-21,17-carbolactone, a compound of claim 1.
7. 6,6-Ethylene-15β,16β-methylene-3-oxo-17α-pregna-1,4-diene-21,17-carbolactone, a compound of claim 1.
8. 6,6-Ethylene-15α,16α-methylene-3-oxo-17α-pregn-4-ene-21,17-carbolactone, a compound of claim 1.
9. 6,6-Ethylene-15α,16α-methylene-3-oxo-17α-pregn-1,4-diene-21,17-carbolactone, a compound of claim 1.
10. 6,6,-Ethylene-18-methyl-15β,16β-methylene-3-oxo-19-nor-17α-pregn-4-ene-21,17-carbolactone, a compound of claim 1.
11. 6,6,-Ethylene-15β,16β-methylene-3-oxo-19-nor-17α-pregn-4-ene-21,17-carbolactone, a compound of claim 1.
12. A pharmaceutical composition comprising an amount of a compound of claim 1 and a pharmacologically acceptable carrier.
13. A composition of claim 12 further comprising a contraceptually effective amount of an estrogen.
14. A composition of claim 12 wherein the amount of said compound is 0.5 to 5 mg.
15. A method of achieving a contraceptive effect in a patient comprising administering an effective amount of a compound of claim 1 to the patient.
16. A method of claim 15 further comprising administering an effective amount of an estrogen to the patient.
17. A method of achieving an aldosterone-antagonistic effect and a gestagenic effect in a patient comprising administering an effective amount of a compound of claim 1 to the patient.
18. A compound of the formula

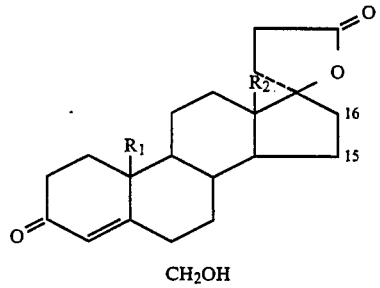

wherein
R₁ is H or CH₃,
R₂ is CH₃ or C₂H₅, and

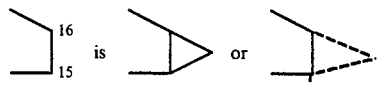

* * * * *